United States Patent
Carman et al.

(10) Patent No.: US 6,284,193 B1
(45) Date of Patent: Sep. 4, 2001

(54) DYNAMIC $O_X$ BIOLOGICAL BURDEN REDUCTION

(76) Inventors: Gary B. Carman, 5815 Lone Horse Dr., Reno, NV (US) 89502; Stephen K. Wirtz, 2230 Figoni Ranch Rd., Sparks, NV (US) 89434

( * ) Notice: Subject to any disclaimer, the term of this patent is extended or adjusted under 35 U.S.C. 154(b) by 0 days.

(21) Appl. No.: 09/217,581

(22) Filed: Dec. 22, 1998

Related U.S. Application Data (60) Provisional application No. 60/068,668, filed on Dec. 23, 1997.

(51) Int. Cl.$^7$ .................................................... A01N 1/00
(52) U.S. Cl. ............................ 422/33; 422/22; 422/23; 422/28; 422/30; 422/33; 422/186.07; 422/292; 210/748
(58) Field of Search ............................... 210/748; 422/22, 422/23, 30, 33, 186.01, 292

(56) References Cited

U.S. PATENT DOCUMENTS

| | | |
|---|---|---|
| 3,068,064 | 12/1962 | McDonald . |
| 3,549,528 | 12/1970 | Armstrong ............................. 210/60 |
| 3,719,017 | 3/1973 | Shapiro et al. ........................... 53/21 |
| 3,897,210 | 7/1975 | Gruber et al. ............................ 21/58 |
| 4,182,663 * | 1/1980 | Vaseeen ................................. 422/22 |
| 4,517,159 | 5/1985 | Karlson ................................. 422/20 |
| 4,640,782 * | 2/1987 | Burleson ............................... 422/22 |
| 4,822,563 | 4/1989 | Joslyn ................................... 422/31 |
| 4,988,484 * | 1/1991 | Karlson .......................... 422/186.07 |
| 5,069,880 * | 12/1991 | Karlson .......................... 422/186.19 |
| 5,120,512 | 6/1992 | Masuda ................................. 422/297 |
| 5,135,721 * | 8/1992 | Richard ................................. 422/22 |
| 5,200,158 * | 4/1993 | Jacob ..................................... 422/22 |
| 5,241,803 | 9/1993 | Griffin ................................... 53/425 |
| 5,344,622 | 9/1994 | Faddis et al. ......................... 422/306 |
| 5,413,758 * | 5/1995 | Caputo et al. .......................... 422/22 |
| 5,518,698 * | 5/1996 | Karlson et al. .................. 422/186.07 |
| 5,702,669 | 12/1997 | Green ..................................... 422/30 |
| 6,066,348 | 5/2000 | Yuan et al. ............................ 426/236 |

* cited by examiner

*Primary Examiner*—Robert J. Warden, Sr.
*Assistant Examiner*—Imad Soubra
(74) *Attorney, Agent, or Firm*—Piper, Marbury, Rudnick & Wolfe, LLP; Laura A. Donnelly (57) ABSTRACT

A method and apparatus for significantly reducing the biological load on consumer products such as food products, botanicals, cosmetic ingredients and medical products is disclosed. The method involves applying a continuous stream of oxygen-containing, i.e., $O_x$, gas to a material in a sealed biological burden reduction chamber. The continuous stream of $O_x$ gas is prepared in an $O_x$ generation cell, which contains a means for generating the $O_x$ gas at a pressure less than 20 lbs/in$^2$ using, for example, one or more of the following: corona discharge, high frequency electrical discharge, ultraviolet light, x-ray, radioactive isotope and electric bear The apparatus contains:

(a) a biological burden reduction chamber;
(b) a vacuum pump coupled to the biological burden reduction chamber;
(c) an $O_x$ generation cell, wherein the $O_x$ generation cell contains an $O_x$ generator capable of generating $O_x$ at a pressure less than 20 lbs/in$^2$;
(d) a first control valve coupled to the biological burden reduction chamber and the $O_x$ generation cell, wherein the first control valve is capable of permitting $O_x$ to be drawn from the $O_x$ generation cell into the biological burden reduction chamber; and
(e) a second control valve coupled to the biological burden reduction chamber, wherein the second control valve is capable of withdrawing $O_x$ contained within the biological burden reduction chamber.

37 Claims, 3 Drawing Sheets

DYNAMIC $O_x$ BIOLOGICAL BURDEN REDUCTION

This application claims priority from U.S. Provisional Application Ser. No. 60/068,668 filed Dec. 23, 1997 (now abandoned).

FIELD OF THE INVENTION

The present invention generally relates to a method and apparatus that can be utilized to significantly reduce the biological load on consumer products such as food products, botanicals, cosmetic ingredients and medical products, which have traditionally been treated with commercial sterilants or fumigants such as ethylene oxide, propylene oxide, methyl bromide, hydrogen phosphide, steam (heat), irradiation, and the like.

BACKGROUND OF THE INVENTION

Currently, ethylene oxide (EO) is the agent of choice for virtually all of the gaseous sterilization of consumer products performed in the United States. EO, however, has a number of properties which limit its use as a sterilant. For example, EO is highly flammable and highly explosive. For this reason, all EO sterilization facilities must include damage-limiting construction and all equipment used in the EO sterilization process must be explosion proof In addition, high concentrations of EO are acutely toxic for humans, and EO has been implicated as a carcinogen in laboratory animals. EO sterilization plants must, therefore, be outfitted with expensive equipment to minimize exposure of facility personnel to EO and to prevent escape of EO to the atmosphere outside the facility.

Another disadvantage of EO is that it reacts with chlorine to form ethylene chlorhydrin (ECH) and with water to form ethylene glycol (EG). Both of these byproducts are toxic and must be reduced to safe levels before sterilized materials are released for use. In fact, formation of ECH and EG preclude the use of EO for sterilization of a number of food products for which it would otherwise be a very useful sterilant.

Over the last fifty years, a number of other gases that lack one or more of the disadvantages of EO have been tested as sterilants. These gases include, for example, hydrogen peroxide, ozone and chlorine dioxide. However, no other gas has proven to be as efficacious as EO for use in large volume industrial sterilizers. The most common reason for failure of these gases as useful sterilants has been inadequate permeation of the gases through packaging materials and into lumens and interstices of the product being sterilized. Failure to permeate may be due to a number of factors including size of the sterilant molecule, reactivity of the sterilant molecule with outer packaging materials prior to reaching the target material, and degradation of the sterilant molecule prior to reaching the target material.

A number of commercial fumigants are presently used to treat foodstuffs and other stored commodities. The most widely used fumigants are methyl bromide, hydrogen phosphide, carbon dioxide, and hydrogen cyanide. Many of these compounds pose hazardous conditions for application personnel and can form deleterious residues in the foodstuffs and commodities that are treated. Methyl bromide, the most widely used fumigant, has been identified as an ozone layer depleting agent and is slated, under the Montreal Protocols of 1997, to be banned by the year 2005. One important factor that differentiates the above listed fumigants from other sterilants is their ability to readily permeate granular or powdered products, which allows the fumgant to contact the infesting pests in such products.

Some of the above-mentioned traditional sterilants or fumigants have been identified with the formation of carcinogens and mutagens which thus limit the products that can be treated.

Other procedures that have been developed to treat products utilize heat, ionizing radiation, and other chemical compounds. All of these procedures are potentially detrimental to the products' nutritional, physical and/or chemical attributes and thus make them undesirable.

Thus, a means to reduce biological loads in consumer products to eliminate human pathogens while maintaining product stability remains a necessity. Accordingly, there remains a need for better alternative methods and apparatus for reducing the biological load on consumer products.

SUMMARY OF THE INVENTION

It is desirable to treat a wide variety of consumer products in chamber type operations in a cost effective manner. The method and apparatus of the present invention permit sterilization or fumigation (hereinafter referred to as "biological burden reduction" of a product in its original container (e.g., burlap bag, fiber drum, kraft paper bag, plastic bag, etc.). Thus, double handling, product loss, and post treatment contamination are reduced.

The method of the present invention utilizes a gaseous mixture containing $O_1$, $O_2$ and $O_3$ (hereinafter referred to as "$O_x$") in a technologically advanced treatment system that overcomes the limitations formerly encountered with $O_3$ treatment on biological burden. Prior $O_3$ treatments include, for example, (1) the submersion of an article to be sterilized in ozone-containing water and the bubbling of ozonated water over the article (see, e.g., U.S. Pat. No. 4,517,159 to Karlson and U.S. Pat. No. 4,640,872 to Burleson); and (2) the static treatment of medical devices and food products with gaseous ozone (see, e.g., U.S. Pat. No. 3,179,017 to Shapiro et al., U.S. Pat. No. 5,069,880 to Karlson, and U.S. Pat. No. 5,120,512 to Masuda.) Systems utilizing ozone as a sterilant such as described above have encountered several limitations. The incorporation of ozone gas into water and then submersion of items(s) to be sterilized or the spraying of ozone treated water onto the surface of item(s) to be sterilized limit the process to products that can be soaked in water. The few gaseous uses of ozone have been limited to the surface treatment of medical devices and the like due to the lack of adequate penetration into compacted products. Thus, although these past processes have proven the efficacy of ozone as a sterilant, the limitation of the use of ozone as a surface treatment has not presented ozone as a reliable sterilant or fumigant for products contained with commercial containers. Furthermore, until recently, high concentration ozone generators, which would have allowed the present invention to properly function, have not been commercially available. The present invention requires a relatively high concentration of $O_x$ for an extended treatment period to assist the required permeation of the $O_x$ into the substrate bring treated. In addition to the generation of the ozone molecule, the present invention also utilizes the quenching effect of other inert gases to assist ozone generation, thereby increasing the stability of the $O_x$ radicals. A combination of oxygen, carbon dioxide, argon, and nitrogen have been used in the method of the present invention to achieve these factors. In addition to the benefits discussed above, the use of small quantities of carbon dioxide results in an increase in the rate of respiration in insects and some microbes, thus further aiding the action of the $O_x$ gases. Furthermore, the presence of atmospheric nitrogen has been utilized in the food industry for many years to protect sensitive oils and fats from oxidative rancidity. Small quantities of nitrogen can be used in the method of the present invention to assist in the protection of sensitive food components as well as assisting in the stabilization of the $O_x$ generation.

As an aid to understanding the invention, but without being limited thereby, the present invention is based on the discovery of the following:

1. That water submersion in $O_3$ sterilization is unnecessary and, in many cases, undesirable;

2. That use of gaseous $O_3$ in a static fashion, in many cases, does not provide adequate penetration of $O_3$ into products being treated;

3. That treating a product in-situ (no repackaging needed) is desirable;

4. That the use of cooler temperatures, in many cases, is desirable; and

5. That the destruction of insects and their eggs is desirable.

Accordingly, it is an object of the present invention to provide a method and apparatus for reducing biological burden from consumer products.

It is another object of the present invention to provide a method and apparatus for reducing biological burden from consumer products in a safe manner.

It is thus an object of the present invention to eliminate the health risks that are associated with the reduction of biological burden from consumer products.

It is a further object of the present invention to provide a simple, efficient and economical method and apparatus for reducing biological burden from consumer products that can be used at the site of production and/or packaging of such products.

In accordance with the above and other objects, the inventive method comprises applying a continuous stream of $O_x$ gas to a material in a sealed biological burden reduction chamber. The continuous stream of $O_x$ gas is prepared in an $O_x$ generation cell, which contains a means for generating the $O_x$ gas at a pressure less than about 20 lbs/in$^2$ using, for example, one or more of the following: corona discharge, high frequency electrical discharge, ultraviolet light, x-ray, radioactive isotope and electron beam.

As discussed herein, a small percentage of $N_2$, $CO_2$ and/or Ar may be added during $O_x$ treatment. The addition of 0% to 15% $N_2$, 1% to 20% $CO_2$ and/or 1% to 18% Ar increases the generation of an $O_x$ quenching effect. Penetration of $O_x$ into the material being treated is thus enhanced. In addition, Argon is unique among the (inert) Noble Gases, in that it is soluble in both water and organic liquids. (The Merck Index Eleventh Edition). This characteristic theoretically enables Argon to become a glue of sorts. Argon is capable of attaching to gases without reacting thereto. Argon thus assists in $O_x$ quenching by attaching to the $O_x$ molecules and preventing the $O_x$ molecules from colliding into each other. Argon also loosely binds hydrophilic and hydrophobic materials, thus allowing one to be diffused through the other, without reacting with either. This characteristic is useful in accelerating the diffusion of $O_x$ into and through hydrophilic materials such as fats, oils and cell walls.

The inventive apparatus comprises:

(a) a biological burden reduction chamber;

(b) a vacuum pump coupled to the biological burden reduction chamber;

(c) an $O_x$ generation cell, wherein the $O_x$ generation cell contains a means for generating $O_x$ at pressure less than about 20 lbs./in 2 using, for example, one or more of the following: corona discharge, high frequency electrical discharge, ultraviolet light, x-ray, radioactive isotope and electron beam;

(d) a first control valve coupled to the biological burden reduction chamber and the $O_x$ generation cell, wherein the first control valve is capable of permitting $O_x$ to be drawn from the $O_x$ generation cell into the biological burden reduction chamber, and (e) a second control valve coupled to the biological burden reduction chamber, wherein the second control valve is capable of withdrawing $O_x$ contained within the biological burden reduction chamber out of the biological burden reduction chamber.

Water vapor may be introduced to the gaseous $O_x$ to maintain an appropriate humidity level, i.e., between about 20% and 98% relative humidity, and, more preferably between about 40% and 75% relative humidity. The appropriate humidity level is dependent upon the ambient humidity and upon the product being treated. For example, granular and powered products require a relatively low humidity level to prevent growth of mold and yeast thereon. However, depending on the length of treatment time, the vacuum created during the process removes humidity, thus requiring the addition of humidity. The $O_x$ gas may then be passed through a commercially available catalytic destruct unit to eliminate any residual $O_3$ and $O_1$ before the gas stream is discharged to the atmosphere.

According to another aspect of the invention, the $O_x$ within the biological reduction chamber is agitated to increase permeation of the $O_x$ into the material being treated. Any means of moving the $O_x$ within the chamber can be used. For example, forced air can be used to distribute the $O_x$ evenly throughout the biological burden reduction chamber.

According to a further aspect of the invention, the $O_x$ in the biological burden reduction chamber is maintained at a concentration of about 0.1% to about 100%, preferably 0.1% to 25%, and more preferably 3% to 16%, per total volume of gases in the biological burden reduction chamber. The amount of $O_x$ employed depends upon the material being treated.

According to yet another aspect of the invention, large biological burden reduction chambers ranging in size from, for example, about 100 ft.$^3$ to about 8000 ft.$^3$ or small biological burden reduction chambers ranging in size from, for example, about 1 ft.$^3$ to about 100 ft.$^3$ may be employed.

According to yet a further aspect of the invention, the water vapor present in the continuous stream of $O_x$ can be controlled prior to applying the continuous stream of $O_x$ to the material being treated.

Preferably, the pressure within the biological burden reduction chamber is maintained at pressure between about 0 psia and 20 psia.

The present invention is also directed to treated consumer products that result from use of the present inventive method and apparatus.

Additional objects and attendant advantages of the present invention will be set forth in the description and examples that follow, or may be learned from practicing the method or using the apparatus of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further objects and attendant advantages, will best be understood by reference to the following detailed description, taken in conjunction with the accompanying drawings.

BRIEF DESCRIPTION OF THE DRAWINGS

In the following description, like parts are designated by like reference numerals throughout the figures.

DESCRIPTION OF PREFERRED EMBODIMENTS

All patents, patent applications and literatures that may be cited herein are incorporated herein by reference.

The antibacterial potential of $O_3$ has been recognized for many years. $O_3$ is widely used as a disinfectant for sewage treatment and for purification of drinking water. It has, however, failed to gain acceptance as a biological burden reduction treatment for medical supplies and consumer goods. The primary reason for this failure is that the $O_3$ molecule is highly unstable and quickly reverts to $O_2$ if it does not encounter a susceptible substrate with which to react. Ozone also has the capacity to react with a broad array of substrates and would be expected to react with packaging materials surrounding the items being sterilized. This further reduces the number of $O_3$ molecules available to react with and inactivate microbial contaminants.

Previous attempts to use $O_3$ as a biological burden reduction treatment include the reliance upon filling a sterilization chamber with $O_3$ and exposing the materials to be treated in static fashion for various periods of time without replenishment of $O_3$. See for example, U.S. Pat. Nos. 3,719,017 and 5,069,880. Under these conditions, the concentration of $O_3$ within the chamber would be expected to rapidly decrease to a level below that required for effective biological burden reduction due to the short half life of $O_3$, which is typically less than 20 minutes. A further disadvantage of the static exposure technology is the reliance on simple diffusion to promote permeation of the $O_3$ molecules through packaging materials and into voids and interstices of the materials being treated. Thus, such methods do not achieve adequate permeation of into the material being treated.

The present invention, which has been designated "dynamic $O_x$ biological burden reduction," offers significant advances over the prior static biological burden reduction technology in that it provides a uniformly high concentration of $O_x$, i.e., between about 3% and 16%, throughout the treatment cycle and promotes rapid permeation of $O_x$ through packaging materials and into the voids and interstices of the materials undergoing treatment. Continuous operation of the vacuum pump and $O_x$ generator during biological burden reduction ensures that the concentration of $O_x$ remains high throughout the process by constantly supplying newly generated $O_x$ molecules to replace those molecules which have spontaneously degraded to inactive $O_2$ and those which have reacted during the process. Operation of the vacuum pump during the process, as practiced in the present invention, also maintains a continuous pressure differential, which actively draws $O_x$ molecules through packaging materials and into the materials being treated.

Dynamic $O_x$ biological burden reduction provides significant cost advantages over existing biological burden reduction technology. The most significant savings derive from the fact that the $O_x$ biological burden reducing gas may be generated on site, during the process.

Because $O_x$ is not flammable or explosive, facilities need not include damage-limiting construction or explosion-proof equipment. Another advantage of dynamic $O_x$ biological burden reduction is that scrubbing will be easily accomplished using existing technology. Moreover, $O_3$ is classified by the U.S. Food and Drug Administration as a generally recognized as safe "GRAS" substance.

The dynamic $O_x$ biological burden reduction process of the invention has proven successful in the treatment of a wide variety of materials, including medical products, spices, flavorings, and packaging materials.

Figure 3:
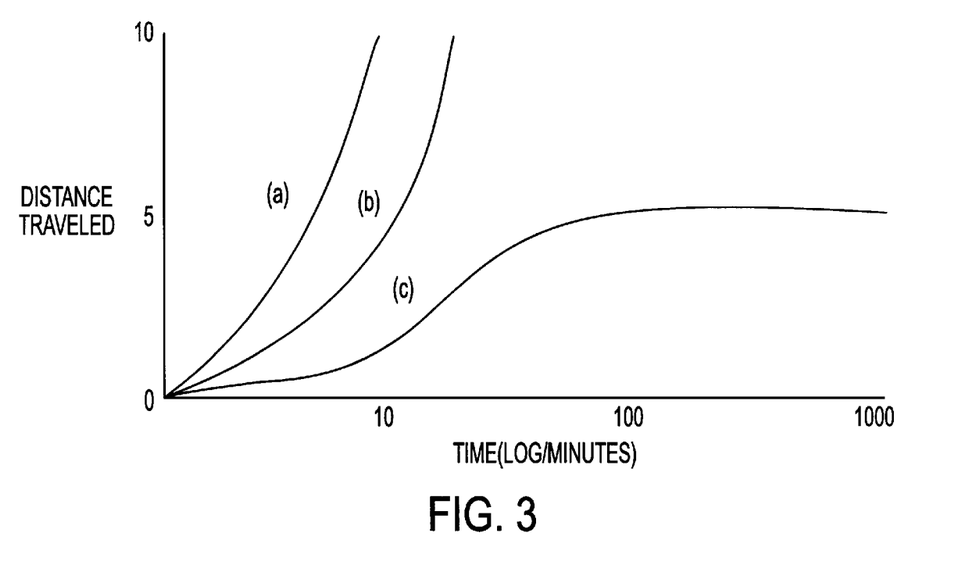
FIG. 3 is a graph comparing permeation of $O_x$ gas for (a) VVP+$CO_2$+$O_x$ in accordance with the method of the invention, (b) VVP+$O_x$ in accordance with the method the invention, and (c) static+$O_x$ in accordance with conventional use of gaseous $O_x$ in a static fashion.

Referring to FIG. 3, which is a graph comparing permeation of $O_x$ gas for (a) VVP+$CO_2$+$O_x$ in accordance with the method of the invention, (b) VP+$O_x$ in accordance with the method the invention and (c) static+$O_x$ in accordance with conventional use of gaseous $O_x$ in a static fashion. The static flow of gas (c) demonstrated a limited permeation, which quickly stopped altogether. The (VVP) process (a) and (b), on the other hand, demonstrated a continuous progression through the packed column; completely depleting the chemical indicator. The method of the present invention enhances the permeability of $O_x$ gases into commercially sized containers of granular and powdered food components. The observation of live insects and microbiological and chemical indicators have been utilized to measure the incorporation of lethal doses of $O_x$ into these containers. Via comparative data (see FIG. 3), a static flow of $O_x$ bearing gas (curve (c)) has shown ineffective in driving the $O_x$ into the containers. The method of the present invention utilizes a process herein described as the Vacuum Vapor Phase Dynamic Flow (VVP). In theory, and supported by empirical evidence, VVP acts as the driving force to enhance permeation of the $O_x$ gases by two factors. The first factor is the molecular acceleration of the $O_x$ gases due to the flashing of the concentrated $O_x$ gas into the reduced pressure treatment chamber. This creates a driving force at a molecular level that continuously forces the $O_x$ gases into the product being treated. The second factor is the resulting reduction of molecules within the reduced pressure treatment chamber which reduces the incidence of molecular collision of the $O_x$ gases. Molecular collision of the $O_x$ gases causes rapid degradation of the $O_3$ and $O_1$ radicals present therein, thereby reducing the gases' effectiveness. Without the VVP process, the $O_x$ gas flow could only be utilized as a surface treatment of non-amorphous materials, therefore, the VVP process expands the capabilities of the present invention to process virtually any type of product in-situ, thus eliminating the need to repackage the product after treatment.

The method of the present invention avoids many of the limitations of previous practices by avoiding the need for water sprays and/or water immersion of the substrate to be treated. Many products such as spices, flour-based products, sugar-based products, cosmetic bases, herbs, and botanicals, which are sensitive to high levels of moisture, can be treated using the method of the present invention. The method of the present invention also avoids the need to open conventional commercial packaging before treatment, thus avoiding unnecessary product degradation and loss. The product is treated in situ utilizing a conventional metal chamber with the product palletized in its normal shipping configuration. Previous methods have required the product to be agitated, blended, bubbled, or re-packaged during or immediately upon completion of the treatment. Due to the increased permeation of the WP process and the $O_x$ gas mixture, these damaging handling practices are avoided. The unique gas mixture also assists in the stabilization of the $O_x$ generation through its quenching effect. The extended half life of the $O_x$ radicals allows the active portions of the treatment gas to fully penetrate the substrate and act upon offending organisms. In combination with carbon dioxide, the stabilized $O_x$ gas mixture is further enhanced by the increased respiration rates of the offending organism(s) while in the presence of the permeated $O_x$ gases. Traditional fumigants and sterilants have required elevated temperatures for prolonged periods of time to be effective. In the case of heat sensitive products such as fruits and spices, the shelf life and/or quality of the product can be severely compromised during such treatment. The method of the present invention protects such products by processing them under relatively cool conditions, i.e, between about 32° F. and 80° F.

Figure 1:
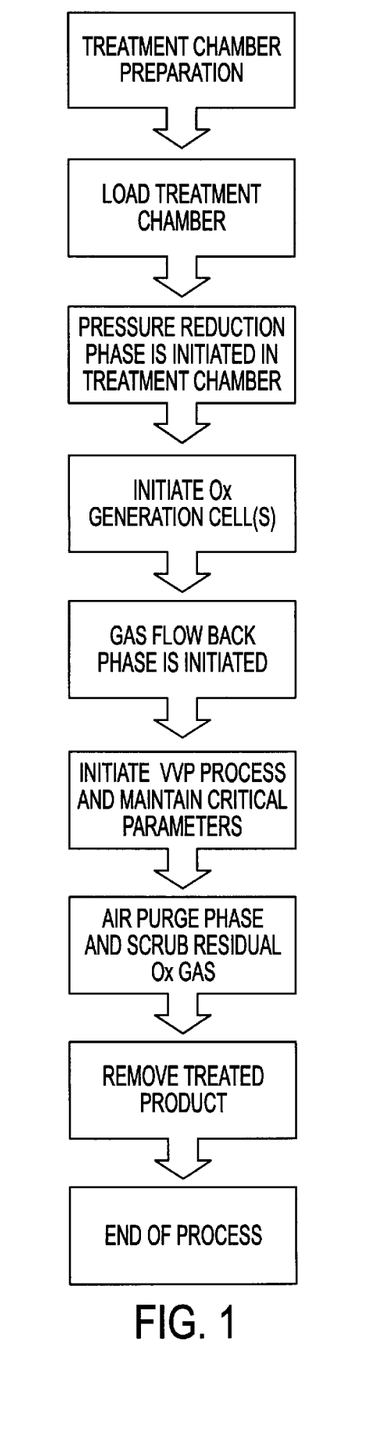
FIG. 1 is a flow chart showing an embodiment of a method for using a continuous flow of $O_x$ to reduce biological burden in accordance with the method of the present invention.
Figure 2:
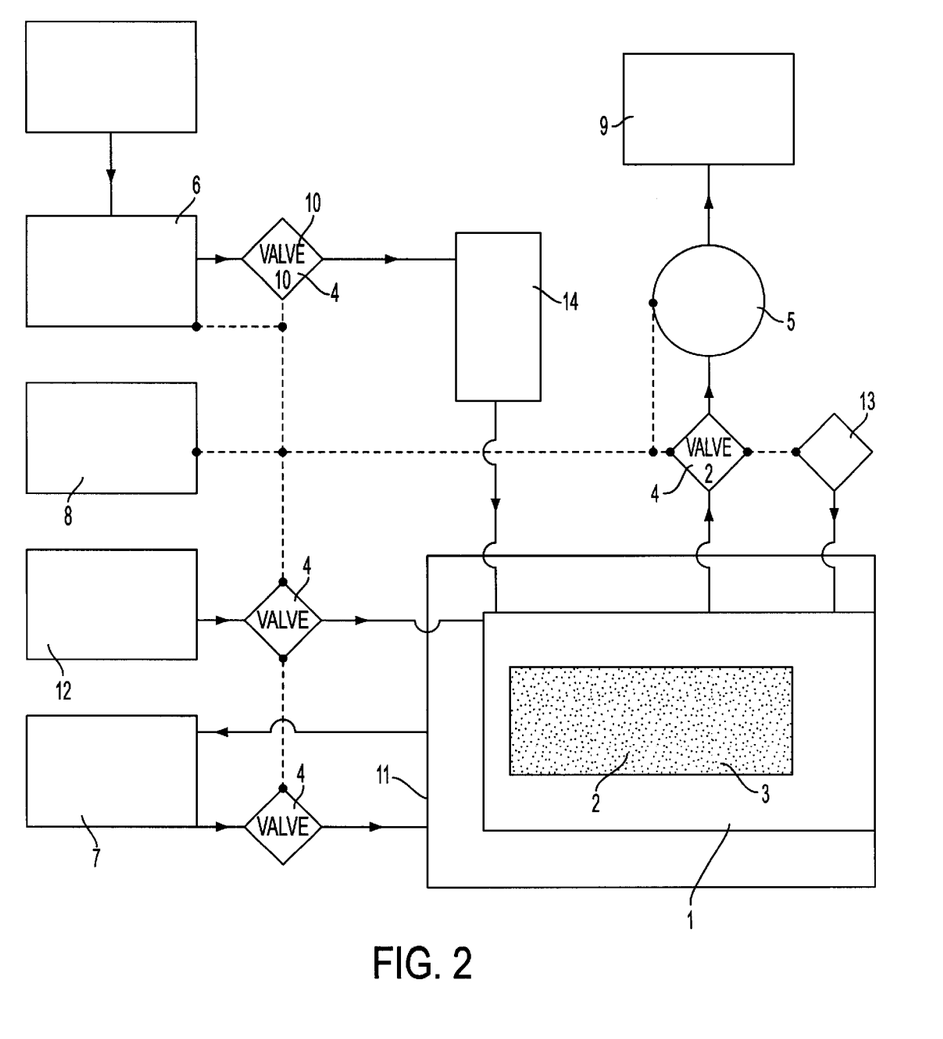
FIG. 2 is a schematic showing one example of an apparatus for using a continuous flow of $O_x$ to reduce biological burden in accordance with the method of the embodiment in FIG. 1.

Referring to FIG. 2, according to an embodiment of the invention, an apparatus according to the invention may include a biological burden reduction chamber 1 equipped with a gasketed door 2 that can be opened to accommodate placement of material 3 within the biological burden reduction chamber 1 and tightly closed and latched. The biological burden reduction chamber 1 perits a vacuum tight seal during the process. The chamber 1 is connected via piping and appropriate control valves 4 to a vacuum pump 5 and separately to a generator of $O_x$ 6, which, in turn is connected to a gas washer 14 and an air preparation regulated feed gas supply 15. The biological burden reduction chamber 1 is jacketed by coils of metal tubing 11 through which heated or chilled water generated by a temperature control (e.g., glycol) system 7 may be pumped to regulate the temperature within the chamber 1 during the biological burden reduction process. The entire biological burden reduction process may be controlled and monitored by a programmable industrial process controller 8. The chamber 1 is also connected to a water vapor source 12 to provide humidity control.

According to the method of the embodiment, material 3 for which biological burden is to be reduced is placed within the biological burden reduction chamber 1 and the door 2 is closed and latched. The process is then initiated by activating the process controller 8, which has previously been programmed with the appropriate process parameters such as pressure, temperature and humidity. The controller 8 first activates the vacuum pump 5 and ancillary valves 4 to reduce the biological burden reduction chamber pressure to a preset level between, e.g., 0 and 20 lbs/in$^2$ depending on the pressure sensitivity of the product being treated, to introduce via the water vapor source 12 the desired humidity, and to maintain a desired temperature via the temperature control system 7. After the appropriate vacuum level has been reached, the controller 8 initiates biological burden reduction by activating the $O_x$ generator 6 and opening a control valve 10, allowing the washed $O_x$ stream to be drawn into, through and out of the chamber 1 by the pressure differential. The vacuum pump 5 and $O_x$ generator 6 operate continuously during the process.

Exposure to the $O_x$ gas mixture may be varied in time from several minutes to several hours, depending on the material being treated. Once the biological burden reduction phase is complete, the vacuum pump 5 and $O_x$ generator 6 are inactivated and fresh air is allowed to enter the chamber 1 via the air purge valve 13. All $O_x$ gases may then be passed through a commercially available catalytic destruct unit 9 which eliminates any residual $O_3$ and $O_1$ before the gas stream is discharged to the atmosphere. The treated material 3 can then be removed from the chamber 1 and is ready for use following appropriate tests to confirm biological burden reduction.

The present invention will be further illustrated by the following non-limiting Examples.

EXAMPLE 1

$O_x$ Treatment of Black Pepper (Piper Nigrum L.) In situ (50 kg Burlap Bags)

| (1) Parameters | |
| --- | --- |
| $O_3$ Concentration (by weight) | 5.4% |
| $CO_2$ Concentration (by weight) | 6.0% |
| Argon Concentration (by weight) | 2.5% |
| Chamber Temperature | 12° C. |
| Relative Humidity | 64% |
| Time (VVP) | 16 hours |
| Pressure | 5.8 p.s.i.a. |

| (2) Results | | |
| --- | --- | --- |
| | Control | VVP Treated |
| Total Plate Count | 5,500,000 | 100,000 |
| Total Coliforms | 5,000 | <10 |
| *Escherichia coli* | 600 | <10 |
| Yeast spp. | 1,500 | <10 |
| Mold spp. | 4,500 | <10 |
| *Bacillus subtilis* (spores) | 1,600,000 | <10 |

Example 2

$O_x$ Treatment of Echinacea Purpurea In situ (50 kg Plastic Woven Bags)

| (1) Parameters | |
| --- | --- |
| $O_3$ Concentration (by weight) | 4.8% |
| $CO_2$ Concentration (by weight) | 9.5% |
| Argon Concentration (by weight) | 3.0% |
| Chamber Temperature | 17° C. |
| Relative Humidity | 70% |
| Time (VVP) | 20 hours |
| Pressure | 4.7 p.s.i.a. |

| (2) Results | | |
| --- | --- | --- |
| | Control | VVP Treated |
| Total Plate Count | 2,300,000 | 180,000 |
| Total Coliforms | 12,000 | 100 |
| *Escherichia coli* | 1,200 | <10 |
| Yeast spp. | 3,400 | <10 |
| Mold spp. | 2,600 | <10 |
| *Bacillus subtilis* (spores) | 1,600,000 | <10 |

EXAMPLE 3

$O_x$ Treatment of Milk Thistle Seed In situ (80 Pound Plastic Woven Bags)

(1) Parameters

| | |
|---|---|
| $O_3$ Concentration (by weight) | 4.5% |
| $CO_2$ Concentration (by weight) | 5.0% |
| Argon Concentration (by weight) | 1.0% |
| Chamber Temperature | 20° C. |
| Relative Humidity | 60% |
| Time (VVP) | 24 hours |
| Pressure | 3.5 p.s.i.a. |

(2) Results

| | Control | VVP Treated |
|---|---|---|
| Total Plate Count | 4,700,000 | 210,000 |
| Total Coliforms | 32,000 | <10 |
| *Escherichia coli* | 5,800 | <10 |
| Yeast spp. | 4,500 | <10 |
| Mold spp. | 16,000 | <10 |
| *Bacillus subtilis* (spores) | 1,600,000 | <10 |

EXAMPLE 4

$O_x$ Treatment of Alfalfa Seed In situ (50 Pound Canvas Bags)

(1) Parameters

| | |
|---|---|
| $O_3$ Concentration (by weight) | 3.5% |
| $CO_2$ Concentration (by weight) | 1.0% |
| Argon Concentration (by weight) | 1.0% |
| Chamber Temperature | 22° C. |
| Relative Humidity | 30% |
| Time (VVP) | 12 hours |
| Pressure | 7.5 p.s.i.a. |

(2) Results

| | Control | VVP Treated |
|---|---|---|
| Total Plate Count | 3,800,000 | 220,000 |
| Total Coliforms | 18,000 | <10 |
| *E. coli* 0157:H | 75,200 | <3 |
| *Bacillus subtilis* (spores) | 1,600,000 | <10 |
| Germination (%) | 96 | 92 |

EXAMPLE 5

$O_x$ Treatment of Navel Oranges for Bean Thrips, Red Scale, and Fuller Rose Beetle

(1) Parameters

| | |
|---|---|
| $O_3$ Concentration (by weight) | 4.0% |
| $CO_2$ Concentration (by weight) | 10.0% |
| Argon Concentration (by weight) | 1.0% |
| Chamber Temperature | 20° C. |
| Relative Humidity | 30% |
| Time (VVP) | 2 hours |
| Pressure | 9.5 p.s.i.a. |

(2) Results

All adults larvae, and eggs (Fuller Rose Beetle only) were killed in the process. The treated fruit was incubated for 28 days after treatment to assure that all three life cycles had been destroyed.

The Bacillus subtilis spore strips are standardized control tabs that are produced by Amsco Medical Products, Erie, Penn., and are used as standards for commercial sterilization processes.

EO and heat have been utilized in the past to de-germ various feed seeds to eliminate the possibility of germination where it is undesirable or would pose a weed growth problem. Certain seed (e.g., safflower), which have been found to be sensitive to EO gas are readily de-germed utilizing the present invention. By controlling certain parameters, some seed types (e.g., alfalfa) have been found to be very resistant to damage by $O_x$ gases, which would lend the present invention to process these seeds for microbiological reduction while still maintaining a high percentage of germination.

The dynamic biological burden reduction process of the invention is thus an excellent substitute for commercial sterilants and fumigants in all of its current uses and is also useful for the treatment of many food ingredients on which commercial sterilant and fumigant use are not permitted, including cocoa beans, grains, and edible gums.

The dynamic $O_x$ biological burden reduction process has also been shown to be highly insecticidal and is therefore a useful substitute for certain current uses of methyl bromnide, which, as discussed herein, is soon to be banned under the direction of the montreal protocols of 1997.

What is claimed:

1. A method for biological burden reduction, comprising a step of applying a continuous stream of $O_x$ gas to a material in a sealed biological burden reduction chamber, wherein a pressure within said sealed biological burden reduction chamber is maintained between 2.91 psia and 14.5 psia, wherein said continuous stream of $O_x$ gas is drawn into, through and out of said biological burden reduction chamber simultaneously throughout said biological burden reduction, and wherein said $O_x$ gas includes $O_1$, $O_2$ and $O_3$.

2. The method of claim 1, wherein said $O_x$ gas is generated in an $O_x$ gas generation cell, a pressure differential between said biological burden reduction chamber and said $O_x$ gas generation cell is created and said pressure differential is maintained while applying said stream of $O_x$ gas to said material.

3. The method of claim 2, further comprising agitating said $O_x$ in said biological burden reduction chamber to increase permeation of said $O_x$ into said material.

4. The method of claim 3, wherein forced air is used to agitate said $O_x$.

5. The method of claim 3, wherein said agitating distributes said $O_x$ evenly throughout said biological burden reduction chamber.

6. The method of claim 2, further comprising:
   (a) creating a vacuum within said biological burden reduction chamber;
   (b) generating $O_x$ gas in said $O_x$ gas generation cell;
   (c) withdrawing a stream of said $O_x$ gas from said $O_x$ gas generation cell into said biological burden reduction chamber; and
   (d) simultaneously withdrawing said $O_x$ gas out of said biological burden reduction chamber.

7. The method of claim 6, wherein said $O_x$ in said biological burden reduction chamber is maintained at a concentration of about 0.1% to about 100% per total volume of gases in said biological burden reduction chamber.

8. The method of claim 7, wherein $O_3$ in said biological burden reduction chamber is maintained at a concentration of about 0.1% to about 25% per total weight of gases in said biological burden reduction chamber.

9. The method of claim 8, wherein said $O_3$ in said biological burden reduction chamber is maintained at a concentration of about 3% to about 16% per total weight of gases in said biological burden reduction chamber, wherein an amount of $O_3$ used is dependent on said material.

10. The method of claim 6, wherein said pressure differential between a pressure within said $O_x$ gas generation cell and a pressure within said biological burden reduction chamber is sufficient to continuously withdraw said $O_x$ gas through said biological burden reduction chamber.

11. The method of claim 10, further comprising controlling water vapor present in said continuous stream of $O_x$ prior to applying said continuous stream of $O_x$ to said material.

12. The method of claim 6, further comprising using a biological burden reduction chamber of about 100 ft.$^3$ to abut 8000 ft.$^3$.

13. The method of claim 6, further comprising using a biological burden reduction chamber of about 1 ft.$^3$ to about 100 ft.$^3$.

14. The method of claim 2, wherein said $O_x$ gas generation cell comprises an $O_x$ gas generator capable of generating $O_x$ gas at a pressure of about 15 psia to about 30 psia.

15. The method of claim 2, wherein a temperature within said biological burden reduction chamber is between about 32° F. and about 80° F.

16. The method of claim 1, wherein said $O_x$ is generated from ambient air or components of ambient air.

17. The method of claim 1, wherein said $O_x$ gas is generated from oxygen sources selected from the group consisting of gaseous oxygen, liquid oxygen, $H_2O$ and mercuric oxide.

18. The method of claim 1, wherein the material is a food product.

19. The method of claim 1, wherein the material is a medical product.

20. The method of claim 1, wherein the material is a cosmetic ingredient.

21. The method of claim 1, wherein the material is a dietary supplement.

22. The method of claim 1, wherein the material is a botanical.

23. The method of claim 1, wherein the material is a nutraceutical.

24. The method of claim 1, wherein the material is a pharmaceutical ingredient.

25. The method of claim 1, wherein the material is a packaging material.

26. The method of claim 1, wherein the material is a nursery stock product.

27. The method of claim 1, wherein the material is a color additive.

28. The method of claim 1, wherein the material is a seed.

29. The method of claim 1, wherein the material is a personal care product.

30. The method of claim 1, wherein the material is an animal feed.

31. The method of claim 1, wherein the material is a flavoring.

32. The method of claim 1, wherein said biological burden is selected from a group of living entities including insects, bacteria, viruses, algae, yeasts, molds, nematodes, parasites and weed seed.

33. The method of claim 1, wherein a humidity of an atmosphere within said biological burden reduction chamber is between about 20% to about 98%.

34. The method of claim 1, wherein a flow rate of said continuous stream of $O_x$ within said biological burden reduction chamber is between about 0.1 L/min/f$^3$ and about 2 L/min/ft$^3$.

35. The method of claim 1, further comprising applying a continuous stream of one or more of a gas selected from the group consisting of $N_2$, $CO_2$ and Ar in addition to said continuous stream of $O_x$.

36. The method of claim 1, wherein said pressure within said biological burden reduction chamber is maintained between about 5.5 psia and about 9 psia.

37. A method for biological burden reduction, comprising a step of applying a continuous stream of $O_x$ gas to a material in a sealed biological burden reduction chamber,
wherein a pressure within said sealed biological burden reduction chamber is maintained between 2.91 psia and 14.5 psia,
wherein said continuous stream of $O_x$ gas is generated by an $O_x$ gas generator, wherein said continuous stream of $O_x$ gas is generated continuously throughout said biological burden reduction,
wherein said sealed biological burden reduction chamber is a closed system that maintains a vacuum tight seal during said biological burden reduction,
wherein said sealed biological burden reduction chamber comprises a vacuum pump, wherein said vacuum pump is operated continuously throughout said biological burden reduction,
wherein said $O_x$ gas generator and said vacuum pump work in unison to draw said continuous stream of $O_x$ gas into, through and out of said biological burden reduction chamber simultaneously throughout said biological burden reduction, and
wherein said $O_x$ gas includes $O_1$, $O_2$ and $O_3$.

* * * * *

UNITED STATES PATENT AND TRADEMARK OFFICE
CERTIFICATE OF CORRECTION

Page 1 of 1

PATENT NO. : 6,284,193 B1
DATED : September 4, 2001
INVENTOR(S) : Carman et al.

It is certified that error appears in the above-identified patent and that said Letters Patent is hereby corrected as shown below:

ABSTRACT,
Line 12, change "bear" to -- beam --.

Signed and Sealed this

Nineteenth Day of March, 2002

Attest:

JAMES E. ROGAN
*Director of the United States Patent and Trademark Office*

*Attesting Officer*